(12) United States Patent
Birnbaum et al.

(10) Patent No.: US 11,848,081 B2
(45) Date of Patent: *Dec. 19, 2023

(54) SYSTEMS AND METHODS FOR AUTOMATIC BIAS MONITORING OF COHORT MODELS AND UN-DEPLOYMENT OF BIASED MODELS

(71) Applicant: Flatiron Health, Inc., New York, NY (US)

(72) Inventors: Benjamin Edward Birnbaum, New York, NY (US); Joshua Daniel Haimson, Brooklyn, NY (US); Lucy Dao-Ke He, New York, NY (US); Melissa Hedberg, New York, NY (US); Nathan Coleman Nussbaum, New York, NY (US); Paul Stephen Richardson, Brooklyn, NY (US); Katharina Nicola Seidl-Rathkopf, New York, NY (US); Evan Eino Estola, Brooklyn, NY (US); Peter Daniel Larson, Brooklyn, NY (US)

(73) Assignee: Flatiron Health, Inc., New York, NY (US)

( * ) Notice: Subject to any disclaimer, the term of this patent is extended or adjusted under 35 U.S.C. 154(b) by 1087 days.

This patent is subject to a terminal disclaimer.

(21) Appl. No.: 16/403,902

(22) Filed: May 6, 2019

(65) Prior Publication Data

US 2020/0058383 A1    Feb. 20, 2020

Related U.S. Application Data

(60) Division of application No. 16/153,678, filed on Oct. 5, 2018, now Pat. No. 11,694,777, which is a
(Continued)

(51) Int. Cl.
*G16H 10/60* (2018.01)
*G06N 20/00* (2019.01)

(52) U.S. Cl.
CPC ............. *G16H 10/60* (2018.01); *G06N 20/00* (2019.01)

(58) Field of Classification Search
CPC ........ G16H 10/60; G16H 50/50; G16H 10/20; G06N 20/00
See application file for complete search history.

(56) References Cited

U.S. PATENT DOCUMENTS

| | | |
|---|---|---|
| 2010/0088264 A1 | 4/2010 | Teverovskiy et al. |
| 2017/0140114 A1 | 5/2017 | Are et al. |

(Continued)

FOREIGN PATENT DOCUMENTS

| | | |
|---|---|---|
| WO | 0077665 A2 | 12/2000 |
| WO | 2004037996 A2 | 5/2004 |

OTHER PUBLICATIONS

Search Report and Written Opinion dated May 7, 2019 issued in International Application No. PCT/US2018/000227, 16 pages.

*Primary Examiner* — Rachelle L Reichert
(74) *Attorney, Agent, or Firm* — Finnegan, Henderson, Farabow, Garrett & Dunner, LLP

(57) ABSTRACT

Systems and methods are disclosed for monitoring models for bias. In one implementation, a system for automatically assessing a deployed model for selection of a cohort may include a processing device programmed to: apply the deployed model to data representing a first plurality of individuals, the data including at least one characteristic of the first plurality of individuals; based on the application, select a subset of the first plurality of individuals as a cohort; receive data representing a second plurality of individuals labeled as within the cohort, the data including the at least one characteristic of the second plurality of individuals;
(Continued)

compare the selected subset and the second plurality of individuals along the at least one characteristic; and determine whether the comparison results in a difference between the selected subset and the second plurality of individuals greater than a threshold.

13 Claims, 8 Drawing Sheets

Related U.S. Application Data continuation of application No. PCT/US2018/000227, filed on Aug. 16, 2018.

(56) References Cited

U.S. PATENT DOCUMENTS

| | | |
|---|---|---|
| 2017/0235871 A1 | 8/2017 | Eden et al. |
| 2021/0193320 A1* | 6/2021 | Shukla .................. G06N 3/084 |

* cited by examiner

SYSTEMS AND METHODS FOR AUTOMATIC BIAS MONITORING OF COHORT MODELS AND UN-DEPLOYMENT OF BIASED MODELS

CROSS REFERENCES TO RELATED APPLICATIONS

This application is a division of U.S. application Ser. No. 16/153,678, filed Oct. 5, 2018, which is a continuation of PCT International Application No. PCT/US2018/000227, filed on Aug. 16, 2018. The entire contents of the foregoing applications are incorporated herein by reference in their entirety.

BACKGROUND

Technical Field

The present disclosure relates to automatic bias monitoring and, more specifically, to automatic monitoring of cohort selection models for bias.

Background Information

The use of models to select cohorts in the medical field creates risks of unintended bias. For example, a machine learned model such as a neural network or the like may inadvertently "learn" that a particular characteristic is important, resulting in systematic exclusion of patients from a cohort. Conversely, a machine learned model such as a neural network or the like may inadvertently "fail to learn" to include subpopulations of interest in a cohort.

Analyses of models for bias is generally performed manually and is therefore time consuming and expensive. Moreover, manual analyses to detect bias do not occur automatically as new data becomes available. Detecting bias within a model may require analysis of medical records associated with hundreds or thousands (or more) of patients included in a cohort selected by the model, where each patient's history may include hundreds or more of pages of clinic notes, radiology reports, pathology reports, doctor or nurse observations, structured and unstructured data, and any other type of information that may be included in a patient's medical record (e.g., an electronic medical record (EMR) or other available data sources (e.g., claims data, patient-reported data)). Secondary characteristics, such as survival rates, the presence of particular biomarkers, or the like may be manually determined in order to detect bias. Not only can such analyses require significant amounts of time, but currently, it also often requires highly trained individuals capable of identifying in patients' medical histories characteristics expected of a cohort and determining secondary characteristics from patients' medical histories. Thus, there is a need to reduce the time required for cohort selection, and a need to reduce the costs associated with cohort selection by reducing the reliance on manual analysis.

SUMMARY

Embodiments consistent with the present disclosure include systems and methods for detecting bias with a model used to select cohorts. Embodiments of the present disclosure may overcome subjective, extant techniques for bias detection with rule-based, automated techniques for performing the same. For example, rules may relate characteristics of interest to a possibility of bias within the model or may relate characteristics of reference groups to a possibility of bias within the model. The use of rules in accordance with embodiments of the present disclosure may thus allow for faster and more efficient detection of bias within a model than using extant techniques. Furthermore, the automated tests performed by embodiments of the present disclosure allow for bias tests not previously performable using manual testing of cohort selection models. In addition, embodiments of the present disclosure may allow for real-time assessment of models as new information becomes available.

In one embodiment, a system for automatically assessing a deployed model for selection of a cohort may comprise at least one processing device. The at least one processing device may be programmed to apply the deployed model to data representing a first plurality of individuals. The data may include at least one characteristic of the first plurality of individuals. The at least one processing device may further be programmed to, based on application of the deployed model, select a subset of the first plurality of individuals as a cohort and receive data representing a second plurality of individuals labeled as within the cohort. The data may include the at least one characteristic of the second plurality of individuals. The at least one processing device may be further programmed to compare the selected subset and the second plurality of individuals along the at least one characteristic and determine whether the comparison results in a difference between the selected subset and the second plurality of individuals greater than a threshold. Additionally or alternatively, the at least one processing device may be programmed to automatically remove the model from deployment when the comparison results in a difference greater than the threshold or when the comparison results in a difference greater than a second threshold, the second threshold being greater than the threshold.

In one embodiment, a system for automatically monitoring a deployed model for selection of a cohort may comprise at least one processing device. The at least one processing device may be programmed to apply the deployed model to data representing a first plurality of individuals. The data may include characteristics of the first plurality of individuals. The at least one processing device may be further programmed to, based on application of the deployed model, select a subset of the first plurality of individuals as a cohort; receive an indication of a characteristic of interest; compare the characteristics of the first plurality of individuals with the characteristic of interest; and determine whether the comparison results in a number of individuals having the characteristic of interest but excluded from the selected subset, and the number is greater than a threshold. Additionally or alternatively, the at least one processing device may be programmed to automatically remove the model from deployment when the comparison results in a number of individuals greater than the threshold or when the comparison results in a number of individuals greater than a second threshold, the second threshold being greater than the threshold.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings.

DETAILED DESCRIPTION

Figure 1:
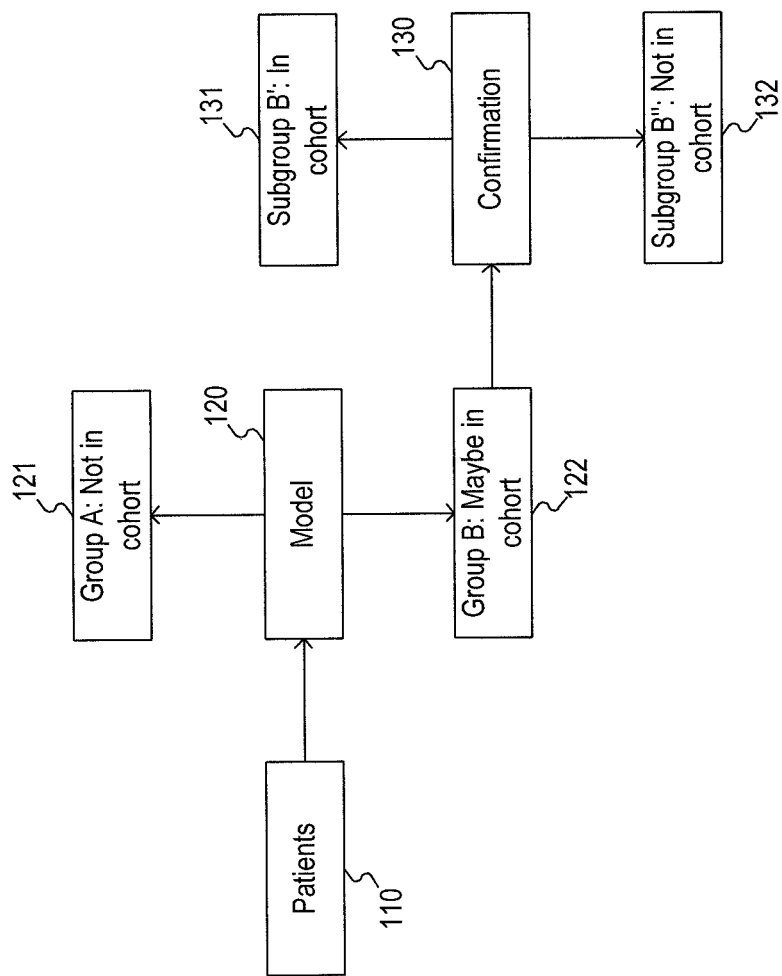
FIG. 1 is a block diagram illustrating a two-step cohort selection filter consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for monitoring models used to select one or more cohorts. A user of the disclosed systems and methods may encompass any individual who may wish to access and/or analyze patient data and/or perform an experiment using a selected cohort. Thus, throughout this disclosure, references to a "user" of the disclosed systems and methods may encompass any individual, such as a physician, a researcher, and/or a quality assurance department at a health care institution.

FIG. 1 illustrates an exemplary two-step cohort selection filter 100. As depicted in FIG. 1, filter 100 may comprise a plurality of patients 110, a portion of which may be viable for inclusion in a cohort. For example, patients 110 may comprise a plurality of breast cancer patients, a portion of which may be metastatic, where metastatic status is an attribute relevant to cohort selection.

Patients 110 may be represented by a plurality of medical records. For example, each patient may be represented by one or more records generated by one or more health care professionals or by the patient. In such an example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases.

In some embodiments, the database may include a plurality of electronic data representations. For example, the patient records may be stored as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

As further depicted in FIG. 1, patients 110 are initially sorted by model 120. For example, model 120 may comprise one or more rules that identify characteristics of patients 110 based on associated medical records and use those characteristics to sort patients 110 into group 121 ("Not in cohort") and group 122 ("Maybe in cohort"). Examples of model 120 may include, but are not limited to, one or more machine learning models, such as the regressions and neural networks described in greater detail with respect to FIG. 4; an automated search for specific phrases combined with structured criteria (e.g., structured recordings of drug administrations) to determine which patients to select; application of rules to the output of natural language processing to determine which patients to select; or the like.

The patients sorted into group 122 may be further processed through confirmation 130. For example, confirmation 130 may comprise a separate model used to sort group 122 into subgroup 131 ("In cohort") and subgroup 132 ("Not in cohort"). Alternatively, confirmation 130 may comprise a manual sorting procedure performed by a medical expert.

As explained above, the use of model 120 to perform an initial sort allows for significant increases in efficiency in cohort selection at least because confirmation 130 is usually a costly and time-consuming process and model 120 reduces the number of patients input to confirmation 130. However, the use of automated rules and/or models in lieu of manual, subjective techniques introduces new technical problems.

For example, automated rules or models that are over-inclusive fail to achieve significant improvements in efficiency in confirmation while imposing upfront costs to develop the automated rules or models. As another example, automated rules or models that are under-inclusive may introduce biases as compared with manual, subjective techniques. Accordingly, embodiments of the present disclosure include solutions to these technical problems of automated initial cohort sorting.

Figure 2:
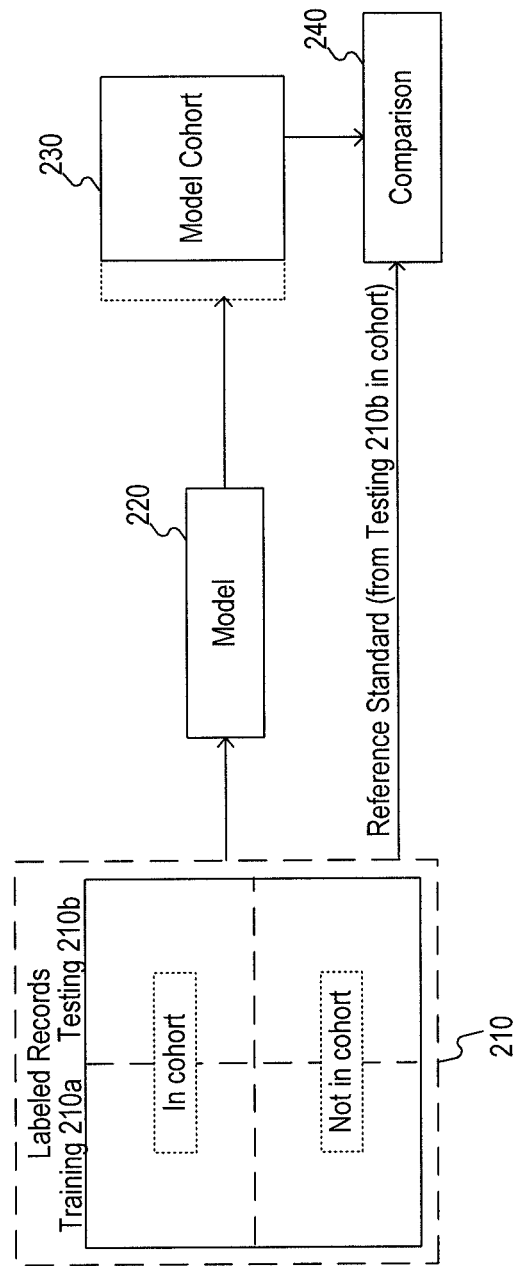
FIG. 2 is a block diagram illustrating an example framework for bias detection within a model consistent with the present disclosure.

FIG. 2 illustrates a framework 200 for bias detection within a model. For example, framework 200 represents an example for monitoring and assessing model 120 of filter 100 of FIG. 1 for bias.

As depicted in FIG. 2, framework 200 may accept, as input, labeled records 210. For example, records 210 may include data associated with a plurality of patients such that each patient is associated with one or more medical records. The labels may, for example, indicate whether the patient is viable for a cohort and may have been determined using other computerized models or using manual annotations from one or more medical professionals or researchers. Model 220 (which may be model 120 of FIG. 1) may extract features from records 210 to produce scores associated with the records 210. Therefore, each patient may have an associated score (e.g., 5 out of 10, 80% probability, 0.8 out of 1.0, "likely" on a scale from "not likely" to "somewhat likely" to "likely" to "very likely," or a similar scale) indicating a likelihood that the patient is a viable candidate for a cohort.

Accordingly, model 220 may produce model cohort 230, which represents one or more patients represented in labeled records 210 selected by the model as candidates for the cohort. As depicted in FIG. 2, not all viable candidates are necessarily selected. For example, as explained below, one or more thresholds of model 220 that affect the sensitivity of model 220 may be set such that the sensitivity is below 100% in order to improve the speed of a confirmation phase (e.g., confirmation 130) of model 220 as compared to manual abstraction. However, this may result in fewer patients being selected for cohort 230 than the total number of viable candidates represented by labeled records 210.

The sensitivity may have been set using trial and error or may have been set using machine learning techniques. Moreover, if bias is detected using framework 200 (as explained below), the sensitivity of model 220 may be automatically increased such that framework 200 may assess whether a higher sensitivity reduces bias in model 220.

As further depicted in FIG. 2, model 220 may only be applied to training records 210a. Accordingly, framework 200 may use records labeled as in the cohort from testing records 210b as a reference standard. The reference standard may be indicative of characteristics and distributions of characteristics that should be present in model cohort 230. This allows for detection of false negatives within model cohort 230, as well as systematic biases resulting in the false negatives. Additionally or alternatively, records labeled as not in the cohort from testing records 210b may be used to assess false positives in model cohort 230.

Thus, comparison 240 may compare particular characteristics of the reference standard to the same characteristics of model cohort 230. For example, comparison 240 may assess whether the distribution of particular characteristics within the reference standard differ from the distribution of those characteristics within model cohort 230. For example, the characteristics may include, but are not limited to, gender, race, age at diagnosis, practice type, number of patient visits, number of follow-up visits, disease stage at diagnosis, or the like. Additionally or alternatively, comparison 240 may determine, based on associated records, one or more derived characteristics of the reference standard and the same derived characteristic(s) for model cohort 230. These derived characteristics may include, but are not limited to, a survival rate, a treatment pattern, a biomarker test rate, or the like. These derived characteristics may be compared similar to the other characteristics described above.

Based on the comparison, an alert may be generated for a user of model 220, alerting the user to the possibility of bias. Additionally or alternatively, the alert may be generated for a creator of model 220, alerting the creator to the possible need to adjust model 220 or to replace model 220 with a new model. The alerts may be generated based on one or more thresholds. For example, particular thresholds applied to differences from the comparison may indicate varying degrees of bias.

Additionally or alternatively, framework 200 may automatically remove model 220 from deployment based on the comparison. For example, model 220 may be de-activated such that it can no longer be used for cohort selection if the differences from the comparison exceed one or more thresholds. The alerts may be combined with automatic removal. For example, one or more lower thresholds may result in alerts while one or more greater thresholds may result in automatic removal of model 220. Accordingly, users and/or creators of models with slight bias may be alerted while models with excessive bias may be automatically removed from use.

Figure 3:
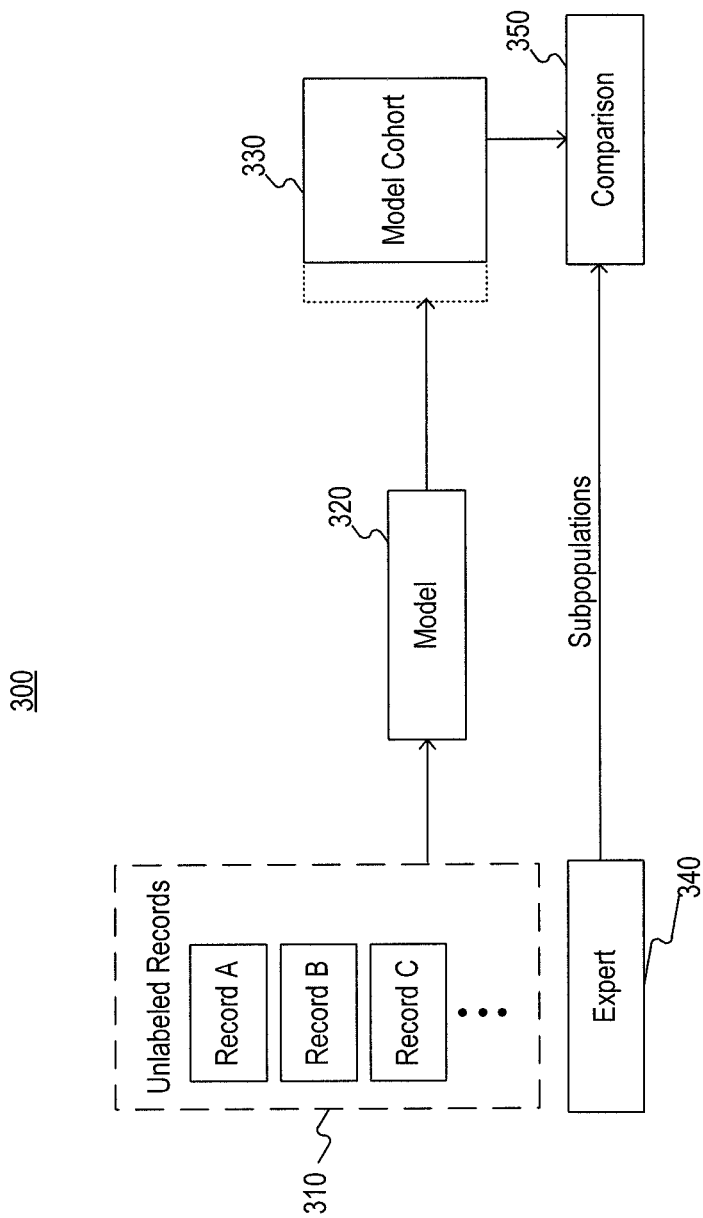
FIG. 3 is a block diagram illustrating another example framework for bias detection within a model consistent with the present disclosure.

FIG. 3 illustrates an example framework 300 for bias detection within a model. For example, framework 300 represents another example for monitoring and assessing model 120 of filter 100 of FIG. 1 for bias. Framework 300 may be used as an alternative or in addition to framework 200, as described below with respect to methods 600 and 700.

As depicted in FIG. 3, framework 300 may accept, as input, unlabeled records 310. For example, records 310 may include data associated with a plurality of patients such that each patient is associated with one or more medical records. Model 320 (which may be model 120 of FIG. 1 and/or model 220 of FIG. 2) may extract features from records 310 to produce scores associated with the records 310. Therefore, each patient may have an associated score (e.g., 5 out of 10, 80% probability, 0.8 out of 1.0, "likely" on a scale from "not likely" to "somewhat likely" to "likely" to "very likely", or a similar scale) indicating a likelihood that the patient is a viable candidate for a cohort.

Accordingly, model 320 may produce model cohort 330, which represents one or more patients represented in unlabeled records 310 selected by the model as candidates for the cohort. As depicted in FIG. 3, not all viable candidates from records 310 are necessarily selected. For example, as explained below, one or more thresholds of model 320 that affect the sensitivity of model 320 may be set such that the sensitivity is below 100% in order to improve the speed of a confirmation phase (e.g., confirmation 130) of model 320 as compared to manual abstraction. However, this may result in fewer patients being selected for cohort 330 than the total number of viable candidates represented by unlabeled records 310.

As explained above, sensitivity may have been set using trial and error or may have been set using machine learning techniques. Moreover, if bias is detected using framework 300 (as explained below), the sensitivity of model 320 may be automatically increased such that framework 300 may assess whether a higher sensitivity reduces bias in model 320.

As further depicted in FIG. 3, framework 300 may receive one or more characteristics indicating subpopulations of interest from an expert 340. For example, the expert 340 may comprise a medical professional or a researcher. Alternatively, the expert 340 may comprise a separate computerized model determining characteristics of subpopulations of interest for the cohort. The characteristics of interest may include, but are not limited to, gender, a disease classification, a number of patient visits, a biomarker, a therapy, or the like.

Thus, comparison 350 may compare the characteristics of interest to the characteristics of patients in records 310. For example, comparison 350 may assess whether one or more patients represented by records 310 includes the characteristics of interest but were excluded from cohort 330. In some embodiments, comparison 240 may determine, based on associated records, one or more derived characteristics of the patients represented by records 310 if one or more of the characteristics of interest are the same derived characteristic(s). These derived characteristics may include, but are not limited to, a diagnosis, an outcome, a biomarker, or the like. These derived characteristics may be used to check for patients that were excluded from cohort 330 similar to the other characteristics described above.

Based on the comparison, an alert may be generated for a user of model 220, alerting the user to the possibility of bias. Additionally or alternatively, the alert may be generated for a creator of model 220, alerting the creator to the possible need to adjust model 220 or to replace model 220 with a new model. The alerts may be generated based on one or more thresholds. For example, particular thresholds applied to the number of patients excluded from cohort 330 but having the characteristic(s) of interest may indicate varying degrees of bias.

Additionally or alternatively, framework 200 may automatically remove model 220 from deployment based on the comparison. For example, model 220 may be de-activated such that it can no longer be used for cohort selection if the number of patients excluded from cohort 330 but having the characteristic(s) of interest exceeds one or more thresholds. The alerts may be combined with automatic removal. For example, one or more lower thresholds may result in alerts while one or more greater thresholds may result in automatic removal of model 220. Accordingly, users and/or creators of models with slight bias may be alerted while models with excessive bias may be automatically removed from use.

As explained below with respect to methods 600 and 700, frameworks 200 and 300 may be combined. In some embodiments, framework 200 and framework 300 may be implemented separately to result in alerts and/or automatic removal of models from deployment. Additionally or alternatively, the assessments from framework 200 and framework 300 may be combined. For example, if the comparison from framework 200 is below a corresponding threshold, and the comparison from framework 300 is below a corresponding threshold, the alert may still be generated and/or the model automatically removed from deployment if both comparisons are above secondary thresholds. Accordingly, two acceptable indicators of bias may combine to result in an unacceptable indicator of bias.

Framework 200 and/or framework 300 may additionally or alternatively generate reports and/or audits that may be used to assess corresponding models, e.g., models 220 and 320. For example, framework 200 and/or 300 may determine the sensitivity of a model (as described above) as compared with its corresponding specificity (e.g., based on a number of characteristics used by the model). Furthermore, the report may include a graph of sensitivity versus specificity and determine the area under the curve for various sets of patients, such as a training set, a test set, one or more other reference sets, or the like, to determine a receiver operating characteristic (ROC) curve. Additionally or alternatively, the report may include a graph showing distribution of scores determined using the model for various sets of patients, such as a training set, a test set, one or more other reference sets, or the like. These graphs may indicate whether one or more thresholds of the model (as described above) are resulting in large exclusions from the cohort.

Additionally or alternatively, the report may include a graph of sensitivity versus one or more characteristics. For example, the report may include a graph of sensitivity versus year of diagnosis. Such a graph may indicate whether newer and/or older diagnoses are biased by the model.

Additionally or alternatively, with respect to subpopulations of interest, the report may include a graph showing distribution of scores determined using the model for one or more subpopulations of interest. Such a graph may indicate whether the model is systematically biased against a subpopulation of interest.

Additionally or alternatively, the report may include one or more graphs of characteristic distributions and/or characteristics over time (e.g., survival probability over time, overall survival over time, time of initial diagnosis, time of follow-up after initial diagnosis, time of advanced diagnosis, time of follow-up after advanced diagnosis, or the like) comparing the reference standard (as described above) to a cohort selected by the model. Such graphs may be used to discern possible bias in the model and trends in the model's performance over time.

Figure 4A:
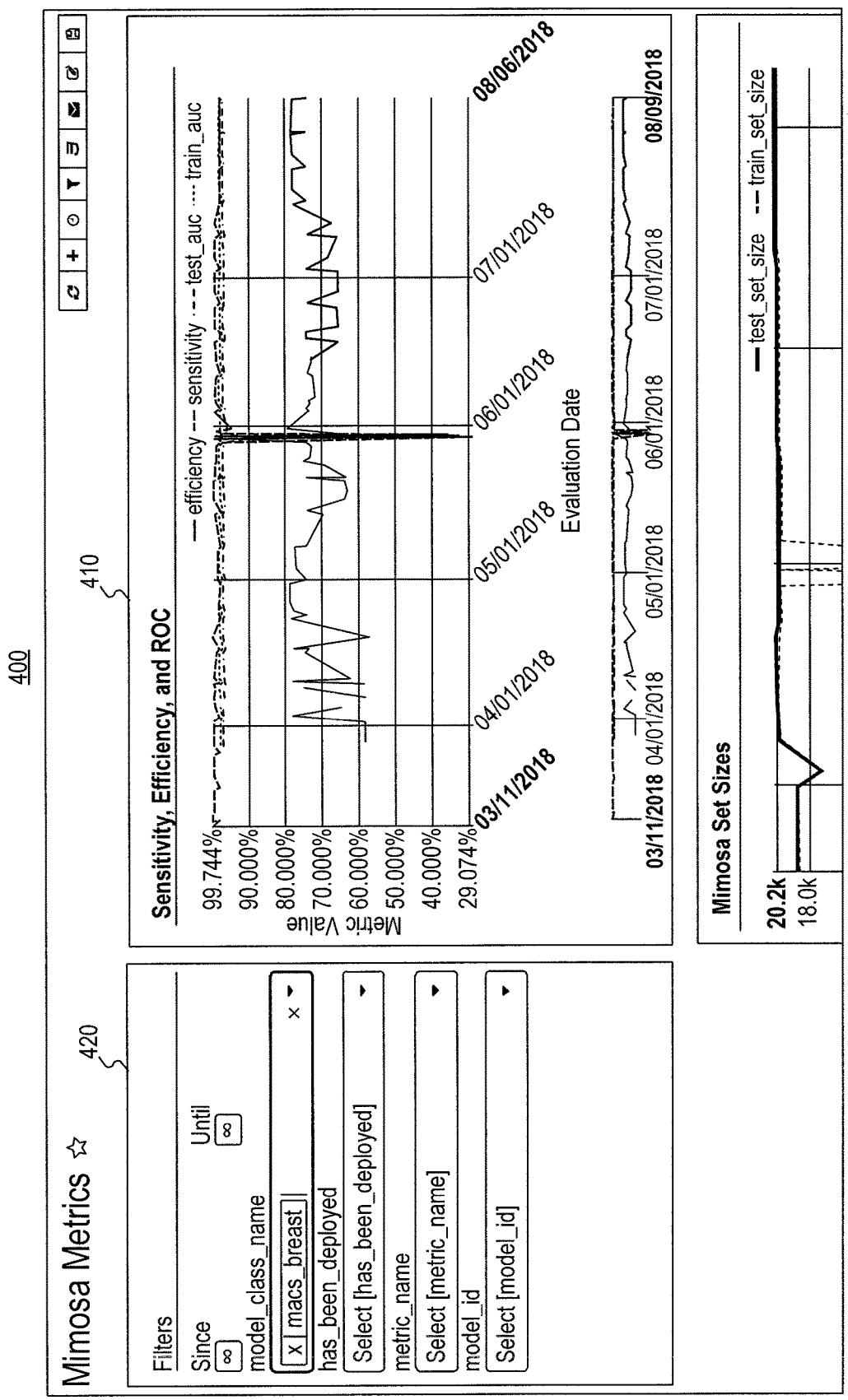
FIG. 4A is a diagram illustrating an example monitoring report consistent with the present disclosure.

FIG. 4A depicts an example of an audit 400 generated, e.g., using framework 200 and/or 300. As depicted in FIG. 4A, audit 400 may include one or more graphs 410, e.g., of ROC, sensitivity, efficiency, or the like, of one or more models across time. Moreover, audit 400 may be customizable, e.g., using controls 420, by time period, by deployment status of the model, or the like. Furthermore, controls 420 may be used to overlay a plurality of models on the same graph 410. Accordingly, the models may be compared across one or more dimensions along the same time period.

Figure 4B:
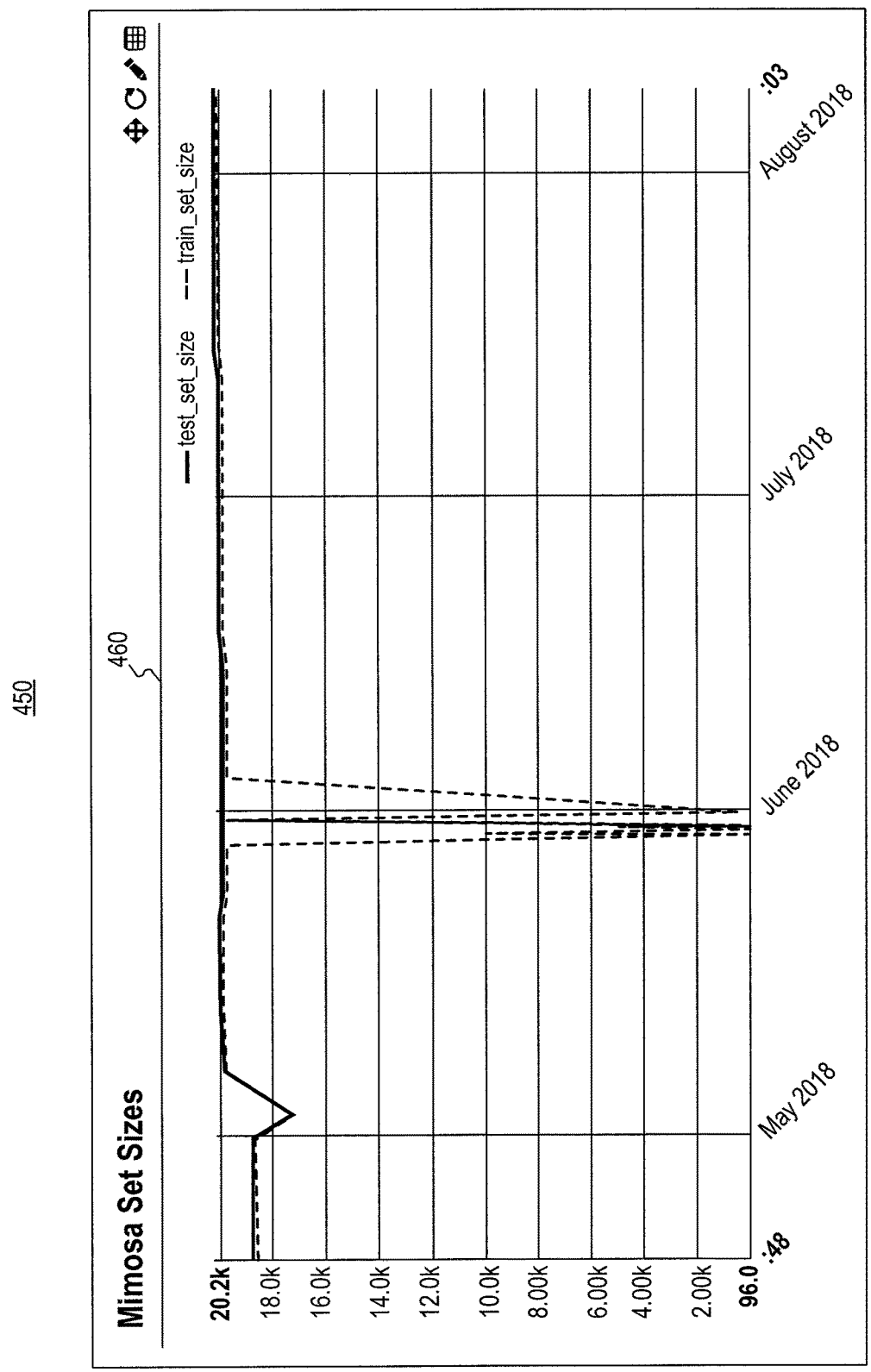
FIG. 4B is a diagram illustrating another example report consistent with the present disclosure.

FIG. 4B depicts another example of an audit 450 generated, e.g., using framework 200 and/or 300. As depicted in FIG. 4B, audit 450 may include one or more graphs 460. As depicted in FIG. 4B, graphs 460 may chart properties of models, such as training set sizes, testing set sizes, reference set sizes, or the like across time. Although not depicted in FIG. 4B, one or more controls similar to controls 420 of FIG. 4A may be used to customize aspects of graph 460 and/or perform overlay of a plurality of models on graph 460. Although depicted as separate, FIG. 4B may represent an audit 450 included in audit 400 of FIG. 4A, e.g., such that graph(s) 460 are visible by scrolling past graph(s) 410.

Figure 5:
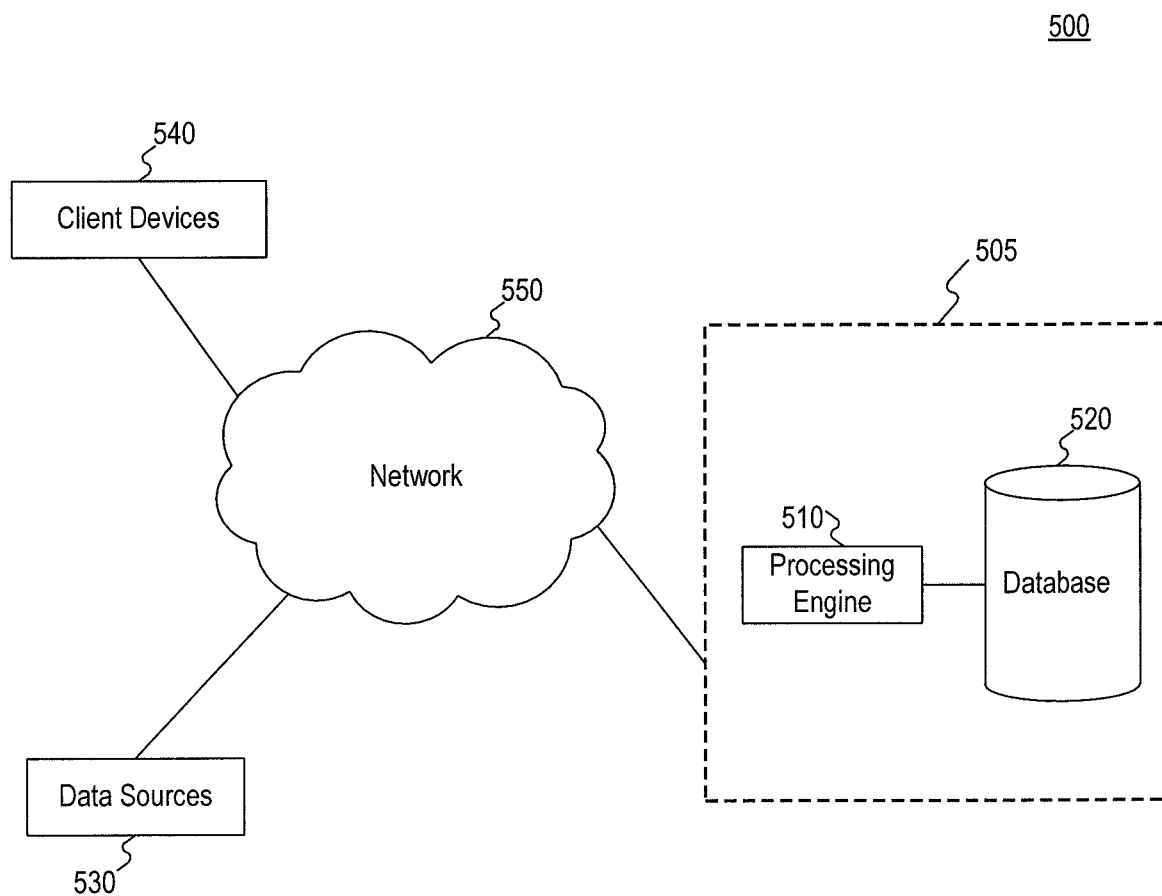
FIG. 5 is a block diagram illustrating an exemplary system environment for implementing embodiments consistent with the present disclosure.

FIG. 5 illustrates an exemplary system environment 500 for implementing embodiments of the present disclosure, such as method 600 of FIG. 6 and/or method 700 of FIG. 7, described below. As shown in FIG. 5, system environment 500 includes several components. It will be appreciated from this disclosure that the number and arrangement of these components is exemplary and provided for purposes of illustration. Other arrangements and numbers of components may be used without departing from the teachings and embodiments of the present disclosure.

As shown in FIG. 5, the exemplary system environment 500 includes a system 505. System 505 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 505 may include a processing engine 510 and one or more databases 520, which are illustrated in a region bounded by a dashed line for system 505 in FIG. 5.

In one embodiment, system 505 may transmit and/or receive patient medical data and/or characteristics of interest to/from various other components, such as one or more data sources 530 and client devices 540. The medical data may be stored in one or more medical records, each medical record associated with a patient. More specifically, system 505 may be configured to receive and store the data transmitted over a network 550 (e.g., Internet, Intranet, WAN, LAN, cellular, etc.) from various data sources, including data sources 530, process the received data, and transmit search results based on the processing to client devices 540.

The various components of system environment 500 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

As described above, system 505 may be configured to receive patient medical records and/or characteristics of interest over a network 550, compare characteristics of a cohort selected by one or more models to characteristics of the received patient records and/or received characteristics of interest, and provide bias probabilities to client devices 540 over the network 550. For example, system 505 may receive patient medical records from data sources 530 or elsewhere on network 550. The records provided to system 505 from data sources 530 (or elsewhere) may include structured data, such as gender, birth year, race, visit date, practice type, insurance carrier and start date, office visits, medication orders, medication administrations, Eastern Cooperative Oncology Group (ECOG) performance status (i.e., ECOG score), weight, lab results, etc.; unstructured data, such as diagnosis date, first activity date, stage at diagnosis, advanced diagnosis date, metastatic diagnosis date (usually for cancer patients), biomarker results, tumor progression and response (usually for cancer patients), oral medications, and laboratory details regarding the lab tests, etc.; and derived data, such as date of death, lines of therapy, and last activity date, outcomes, etc. In one embodiment, the unstructured data may be captured by an abstraction process, while the structured data may be entered by the health care professional or calculated using algorithms. In one embodiment, data sources 530 may include medical care providers (e.g., physicians, hospitals), laboratories, insurance companies, and any other source of patient data.

System 505 may also communicate with client devices 540 over network 550. For example, client devices 530 may transmit queries for patient medical records over network 550 to system 505. In one embodiment, a query for the records may include patient characteristics, such as patient identifier (ID), biomarker status, stage, drug/line combination, lines of therapy, age range at advanced diagnosis, date of advanced diagnosis, an indicator from whence the test sample came, details on the actual Epidermal Growth Factor Receptor (EGFR) mutation, an indicator from whence the test tissue was collected (for cancer tests), type of assay, staining intensity, if metastasized and if spread (for cancer patients), etc. Alternatively, a query for the records may include a query for records manually annotated as within a cohort for comparison to the records of individuals selected as within the cohort by one or more models. System 505 may query database 520 to identify one or more patients matching the query parameters and transmit medical records associated with the matching patient(s) over network 550 to client devices 540.

In accordance with certain embodiments, system 505 may include one or more processing engines 510, which may be configured to transmit medical records over network 550 to and from data sources 530 and client devices 540. In one embodiment, each processing engine 510 may store records received from data sources 530 and client devices 540 in one or more databases 520. Databases 520 may be any suitable combination of large scale data storage devices, which may optionally include any type or combination of slave databases, load balancers, dummy servers, firewalls, back-up databases, and/or any other desired database components. Each processing engine 510 may also access data stored by databases 520 to process queries received from client devices 540. For example, processing engine 510 may access from databases 520 patient data (e.g., patient medical records) received from data sources 530 and generate a user interface that visualizes the patient data (e.g., on a timeline) in a standardized format. Processing engine 510 may transmit the generated user interface to client device 540 for visualization of one or more patient records.

As discussed above, system 500 may exchange data, and such exchanges may occur over a data interface. As used herein, a data interface may include any boundary across which two or more components of system 500 exchange data. For example, system 500 may exchange data between software, hardware, databases, devices, humans, or any combination of the foregoing. Furthermore, it will be appreciated that any suitable configuration of software, processors, data storage devices, and networks may be selected to implement the components of system environment 500 and features of related embodiments.

In some embodiments, system 505 may select one or more cohorts. As used herein, a cohort may include any grouping of data (people, articles, objects, etc.) that shares at least one common characteristic or that exhibit attributes meeting a predefined set of criteria. In some embodiments, a cohort may include individuals that exhibit at least one common characteristic from a medical perspective (e.g., demographic or clinical characteristics). An individual may include any member of one or more groups (e.g., objects, people, articles, etc.). For example, those individuals from a population determined to have a certain type of disease, or more specifically, certain characteristics associated with that disease (e.g., breast cancer in stage IV) may be identified and placed in a common cohort. Cohorts may be assembled for various purposes. In some instances, cohorts may be assembled to form groups used to analyze the characteristics of certain diseases, such as their epidemiology, treatment approaches, how outcomes such as mortality or progression of disease depend on certain variables, or the like.

Additionally, the performance of the model-assisted cohort selection system may be continuously monitored to avoid bias. For example, system 505 may use a labeled data set for which a desired outcome is already known. Such data may be referred to as "reference standard" and may be generated, for example, through an abstraction process in which all of the individuals of a particular population are screened relative to one or more cohorts, and each individual is assigned to an appropriate cohort. Such a process may allow for monitoring whether individuals are systematically excluded from a cohort—something that may result in undesirable biasing of the cohort, as explained above. Additionally or alternatively, system 505 may receive characteristics of interest that define one or more subpopulations that should be included in the cohort. This processor may allow for ensuring that the model captures individuals particularly suited for the cohort—if not, the model may suffer from undesired biasing, as explained above.

System behavior and performance may be monitored against various metrics. In some instances, the sensitivity of the trained system may be monitored to determine whether the system is capturing all or substantially all of the individuals from a particular population that should be included in a particular cohort. Additionally, or alternatively, the efficiency of the system may be monitored to determine an achieved reduction (e.g., a percentage reduction) in the number of individuals required to proceed to an abstraction process. In some embodiments, the trained model may provide a sensitivity level of 95% or higher, meaning that less than 5% of individuals from a particular population that should be included in a particular cohort are omitted from the cohort. In some cases, the trained system may provide efficiency levels of 50% or more, meaning that half or less of a particular population would require abstraction subsequent to operation of the model-assisted cohort selector. Such efficiencies may be realized where the model-assisted system generates a confidence level or score high enough for certain individuals to conclude that those individuals do not belong in a particular cohort. In such instances, abstraction for those individuals may not be required. For the remaining individuals in a population not excluded from the cohort by the model-assisted selector, abstraction may be employed to confirm whether inclusion of those individuals into the cohort is appropriate.

The selection criteria of the model may be varied to achieve desired selectivity and/or efficiency levels. For example, where the selection criteria are made less rigorous, fewer individuals in a given population may be excluded from the cohort by the model-assisted system, and more cohort candidates may be identified. In such a case, the sensitivity may rise, as fewer individuals that should be included in the cohort would be lost from the cohort as a result of automatic selection. In such cases, however, the abstraction reduction efficiency may decline, as more individuals may be required to go through an abstraction process to confirm their placement into the cohort. On the other hand, if the selection criteria are made more rigorous, then more individuals could potentially be identified as inappropriate for the cohort. In such cases, the abstraction efficiency may rise, as few individuals would be required to proceed to an abstraction process. More rigorous selection criteria, however, may result in a reduction in sensitivity, meaning that the cohort may ultimately be under-inclusive.

Figure 6:
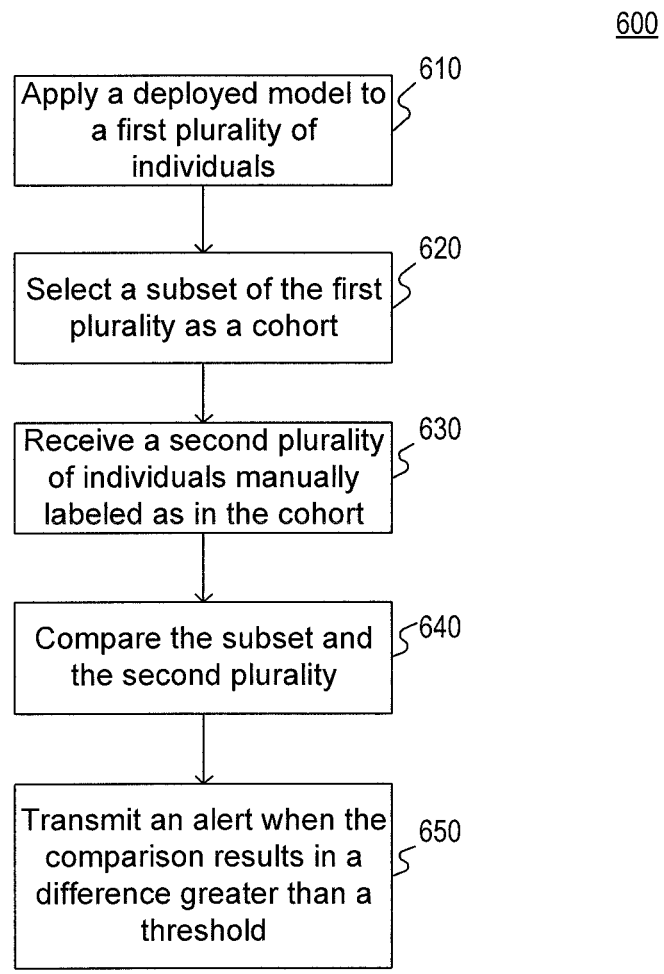
FIG. 6 is a flowchart illustrating an exemplary method for assessing a deployed model for selection of a cohort consistent with the present disclosure.

FIG. 6 illustrates an exemplary method 600 for assessing a deployed model for selection of a cohort. The deployed model may be executed by at least one of a medical device or a server associated with a healthcare facility. For example, a server associated with a healthcare facility may include an on-premise server, a server owned and operated by the healthcare facility but located remotely therefrom, a remote server comprising a portion of a cloud computing service or other remote computing server to which the healthcare facility subscribes, or the like. Method 600 may be implemented, for example, by processing engine 510 of system 500 of FIG. 5. Processing engine 510 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

At step 610, the at least one processing device may apply the deployed model to data representing a first plurality of individuals. As explained above, the data may include at least one characteristic of the first plurality of individuals. For example, the at least one characteristic includes at least one of gender, race, age at diagnosis, practice type, number of patient visits, number of follow-up visits, or disease stage at diagnosis. As explained above with respect to FIG. 2, the data may comprise labeled records representing the first plurality of individuals. Alternatively, the data may comprise unlabeled records representing the first plurality of individuals.

In some embodiments, the at least one processing device may further determine, based on the at least one characteristic, at least one derived characteristic for the selected subset and the second plurality of individuals. For example, the at least one derived characteristic may include at least one of a survival rate, a treatment pattern, or a biomarker test rate.

At step 620, the at least one processing device may, based on application of the deployed model, select a subset of the first plurality of individuals as a cohort. At step 630, the at least one processing device may receive data representing a second plurality of individuals labeled as within the cohort. As explained above, the data may include the at least one characteristic of the second plurality of individuals. Moreover, as explained above with respect to FIG. 2, the data may comprise labeled records representing the second plurality of individuals. For example, the second plurality of individuals may comprise a reference standard derived from the same labeled records as the first plurality of individuals. Alternatively, the second plurality of individuals may comprise a reference standard derived from labeled records for comparison to the first plurality of individuals represented by unlabeled records.

At step 640, the at least one processing device may compare the selected subset and the second plurality of individuals along the at least one characteristic. For example, the comparison may involve determination of differences between distributions of the at least one characteristic in the selected subset and the second plurality of individuals. Accordingly, if the selected subset is 60% female but the second plurality of individuals is 58% female, the difference may comprise 2% in gender distribution.

In embodiments where at least one derived characteristic is determined, the comparison may further include comparing the selected subset and the second plurality of individuals along the at least one derived characteristic. For example, the comparison may involve determination of differences between distributions of the at least one derived characteristic in the selected subset and the second plurality of individuals. Accordingly, if the selected subset has a particular survival probability over time and the second plurality of individuals has a particular survival probability over time that is within a range defined by the particular survival probability over time of the selected subset, the difference may be determined as zero. Otherwise, the distance between the survival probabilities over time may be determined and averaged over time to compute the difference. Other determinations of differences between two scatter plots of data may additionally or alternatively be used.

At step 650, the at least one processing device may determine whether the comparison results in a difference between the selected subset and the second plurality of individuals greater than a threshold. Furthermore, when the comparison results in a difference between the selected subset and the second plurality of individuals greater than a second threshold, the at least one processing device may transmit an alert to a user of the deployed model. For example, the alert may comprise an email, an automated phone call, an automated text message, or other indicator that alerts the user to the possible presence of bias. The alert may include the difference measure from the comparison or may include a probability of bias determined from the difference measure. In some embodiments, the at least one processing device may additionally or alternatively transmit the alert to a creator of the deployed model. Additionally with or alternatively to an alert, when the comparison results in a difference between the selected subset and the second plurality of individuals greater than a second threshold, the at least one processing may generate a report including results of the comparison, e.g., as explained above with respect to FIGS. 4A and 4B. In some embodiments, the at least one processing device may store the report for access by a user of the deployed model.

Additionally or alternatively, the at least one processing device may automatically remove the model from deployment when the comparison results in a difference between the selected subset and the second plurality of individuals greater than a threshold. Alternatively, the thresholds may be tiered such that an alert is transmitted when the difference is greater than the threshold and the model is automatically removed from deployment when the difference is greater than a second threshold, the second threshold being greater than the threshold. In any of the embodiments described above, automatically removing the model may include instructing the medical device or the server to stop executing the deployed model.

Method 600 may further include additional steps. For example, method 600 may be performed iteratively in order to re-assess the model in real-time when new information is available. In one example, the model may be assessed each time new individuals are selected for the cohort. For example, the at least one processing device may apply the deployed model to data representing a third plurality of individuals, the data including the at least one characteristic of the third plurality of individuals; based on application of the deployed model, select a subset of the third plurality of individuals as a cohort; compare the selected subset of the third plurality of individuals and the second plurality of individuals along the at least one characteristic; and when the comparison results in a difference between the selected subset of the third plurality of individuals and the second plurality of individuals greater than the threshold, transmit the alert to the user of the deployed model. Additionally or alternatively, the model may be assessed each time new reference standards are available. For example, the at least one processing device may receive data representing a third plurality of individuals labeled as within the cohort, the data including the at least one characteristic of the third plurality of individuals; compare the selected subset and the third plurality of individuals along the at least one characteristic; and when the comparison results in a difference between the selected subset and the third plurality of individuals greater than the threshold, transmit the alert to the user of the deployed model. In any of these examples, the model may be removed from deployment based on the threshold and/or a second, larger threshold, as explained above with respect to step 650. Moreover, in any of the embodiments described above, method 600 may include generation of one or more reports and/or one or more audits, as described above, e.g., with respect to FIGS. 4A and 4B.

Figure 7:
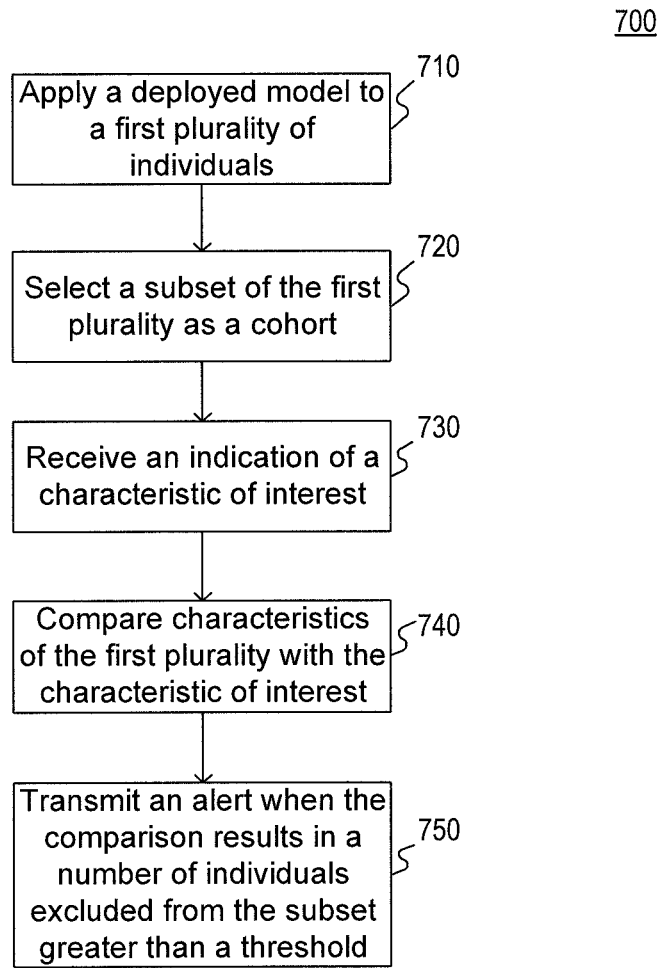
FIG. 7 is a flowchart illustrating another exemplary method for assessing a deployed model for selection of a cohort consistent with the present disclosure.

FIG. 7 illustrates an exemplary method 700 for assessing a deployed model for selection of a cohort. The deployed model may be executed by at least one of a medical device or a server associated with a healthcare facility. For example, as explained above, a server associated with a healthcare facility may include an on-premise server, a server owned and operated by the healthcare facility but located remotely therefrom, a remote server comprising a portion of a cloud computing service or other remote computing server to which the healthcare facility subscribes, or the like. Method 700 may be implemented, for example, by processing engine 510 of system 500 of FIG. 5. Processing engine 510 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

At step 710, the at least one processing device may apply the deployed model to data representing a first plurality of individuals. As explained above, the data may include characteristics of the first plurality of individuals. For example, characteristics may include at least one of gender, race, age at diagnosis, practice type, number of patient visits, number of follow-up visits, or disease stage at diagnosis. As explained above with respect to FIG. 2, the data may comprise labeled records representing the first plurality of individuals. Alternatively, the data may comprise unlabeled records representing the first plurality of individuals.

In some embodiments, the at least one processing device may further determine, based on the characteristics, at least one derived characteristic for the first plurality of individuals. For example, the at least one derived characteristic includes at least one of a diagnosis, an outcome, or a biomarker. In some embodiments, the at least one processing device may determine the at least one derived characteristic with analysis of unstructured data included in the data representing the first plurality of individuals.

At step 720, the at least one processing device may, based on application of the deployed model, select a subset of the first plurality of individuals as a cohort. At step 730, the at least one processing device may receive an indication of a characteristic of interest. For example, the characteristic of interest may include at least one of gender, a disease classification, a number of patient visits, a biomarker, or a therapy.

At step 740, the at least one processing device may compare the characteristics of the first plurality of individuals with the characteristic of interest. For example, the comparison may involve determination of individuals in the first plurality with associated data including the characteristic of interest but excluded from the subset determined in step 720.

In embodiments where at least one derived characteristic is determined, the comparison may further include comparing the at least one derived characteristic of the first plurality of individuals with the characteristic of interest. Similar to the comparison described above, the comparison may involve determination of individuals in the first plurality with associated data including the characteristic of interest but excluded from the subset determined in step 720.

At step 750, the at least one processing device may determine whether the comparison results in a number of individuals having the characteristic of interest but excluded from the selected subset, and the number is greater than a threshold. Furthermore, when the number is greater than the threshold, the at least one processing device may transmit an alert to a user of the deployed model. For example, the alert may comprise an email, an automated phone call, an automated text message, or other indicator that alerts the user to the possible presence of bias. The alert may include the number of excluded individuals from the comparison or may include a probability of bias determined from the number of individuals. In some embodiments, the at least one processing device may additionally or alternatively transmit the alert to a creator of the deployed model. Additionally with or alternatively to an alert, when the number is greater than the threshold, the at least one processing may generate a report including results of the comparison, e.g., as explained above with respect to FIGS. 4A and 4B. In some embodiments, the at least one processing device may store the report for access by a user of the deployed model.

Additionally or alternatively, the at least one processing device may automatically remove the model from deployment when the comparison results in a number of individuals having the characteristic of interest but excluded from the selected subset, and the number is greater than a threshold. Alternatively, the thresholds may be tiered such that an alert is transmitted when the number of individuals is greater than the threshold and the model is automatically removed from deployment when the number of individuals is greater than a second threshold, the second threshold being greater than the threshold. In any of the embodiments described above, automatically removing the model may include instructing the medical device or the server to stop executing the deployed model.

Method 700 may further include additional steps. For example, method 700 may be performed iteratively in order to re-assess the model in real-time when new information is available. In one example, the model may be assessed each time new individuals are selected for the cohort. For example, the at least one processing device may apply the deployed model to data representing a second plurality of individuals, the data including characteristics of the second plurality of individuals; based on application of the deployed model, select a subset of the second plurality of individuals as a cohort; compare the characteristics of the second plurality of individuals with the characteristic of interest; and when the comparison results in a number of individuals having the characteristic of interest but excluded from the selected subset, and the number is greater than a threshold, transmit the alert to the user of the deployed model. Additionally or alternatively, the model may be assessed each time new characteristics of interests are available. For example, the at least one processing device may receive an indication of a second characteristic of interest; compare the characteristics of the first plurality of individuals with the second characteristic of interest; and when the comparison results in a number of individuals having the second characteristic of interest but excluded from the selected subset, and the number is greater than a threshold, transmit the alert to the user of the deployed model. In any of these examples, the model may be removed from deployment based on the threshold and/or a second, larger threshold, as explained above with respect to step 750. Moreover, in any of the embodiments described above, method 700 may include generation of one or more reports and/or one or more audits, as described above, e.g., with respect to FIGS. 4A and 4B.

In some embodiments, methods 600 and 700 may be combined. For example, the at least one processing device may assess the model against reference standards as well as any received characteristics of interest. In some embodiments, these assessments may be performed separately to result in alerts and/or automatic removal of models from deployment. Additionally or alternatively, these assessments may be combined. For example, if the comparison from a reference standard assessment is below a corresponding threshold, and the comparison from a characteristic of interest assessment is below a corresponding threshold, the system may still generate an alert and/or automatically remove the model from deployment if both comparisons are above secondary thresholds. Accordingly, two acceptable indicators of bias may combine to result in an unacceptable indicator of bias.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for automatically monitoring a machine learning model for selection of a cohort, the system comprising:
at least one processing device programmed to:
train a machine learning model to select individuals for a cohort, the machine learning model including a neural network and being trained using a training data set of a plurality of labeled medical records, wherein each labeled medical record of the plurality of labeled medical records:
includes a plurality of patient characteristics associated with a corresponding individuals, and
is labeled to indicate a desired outcome for whether the corresponding individual is included in the cohort;
apply the machine learning model to data representing a first plurality of individuals, the data including characteristics of the first plurality of individuals;
based on application of the machine learning model, select a subset of the first plurality of individuals as the cohort;
receive an indication of a characteristic of interest of the plurality of patient characteristics;
determine, based on the data representing the first plurality of individuals, a number of the first plurality of individuals that are associated with the characteristic of interest but are not included in the selected subset;
compare the number of the first plurality of individuals to a first threshold and a second threshold, the second threshold being greater than the first threshold;
based on a determination that the number of the first plurality of individuals exceeds the first threshold and not the second threshold, transmit an alert to a user of the machine learning model; and
based on a determination that the number of the first plurality of individuals exceeds the first threshold and the second threshold, automatically adjust at least one aspect of the machine learning model.

2. The system of claim 1, wherein the characteristic of interest includes at least one of gender, a disease classification, a number of patient visits, a biomarker, or a therapy.

3. The system of claim 1, wherein the at least one processing device is further programmed to determine, based on the characteristics, at least one derived characteristic for the first plurality of individuals.

4. The system of claim 3, wherein the at least one derived characteristic includes at least one of a diagnosis, an outcome, or a biomarker.

5. The system of claim 3, wherein the at least one processing device is further programmed to determine the at least one derived characteristic with analysis of unstructured data included in the data representing the first plurality of individuals.

6. The system of claim 1, wherein the machine learning model is executed by at least one of a medical device or a server associated with a healthcare facility.

7. The system of claim 1, wherein the at least one processing device is further programmed to:
apply the machine learning model to data representing a second plurality of individuals, the data including characteristics of the second plurality of individuals;
based on application of the machine learning model, select a subset of the second plurality of individuals;
determine, based on the data representing the second plurality of individuals, a number of the second plurality of individuals that are associated with the characteristic of interest but are not included in the selected subset of the second plurality of individuals;
compare the number of the second plurality of individuals associated with the characteristic of interest but not included in the selected subset of the second plurality of individuals to the first threshold; and
based on a determination that the number of the second plurality of individuals having the characteristic of interest but excluded from the selected subset of the second plurality of individuals exceeds the first threshold, transmit the alert to the user of the machine learning model.

8. The system of claim 1, wherein the at least one processing device is further programmed to:
receive an indication of a second characteristic of interest of the plurality of patient characteristics;
determine, based on the data representing the first plurality of individuals, a number of the first plurality of individuals that are associated with the second characteristic of interest but are not included in the selected subset;
compare the number of the first plurality of individuals associated with the second characteristic of interest but not included in the selected subset to the first threshold; and
based on a determination that the number of the first plurality of individuals having the second characteristic of interest but excluded from the selected subset exceeds the first threshold, transmit the alert to the user of the machine learning model.

9. The system of claim 1, wherein the automatic adjustment of the machine learning model includes increasing a sensitivity of the machine learning model.

10. The system of claim 1, wherein the at least one processing device is further programmed to generate a report including a comparison of a sensitivity and an efficiency of the machine learning model.

11. The system of claim 10, wherein generating the report includes displaying a graphical user interface including the report, the graphical user interface including one or more controls to customize at least one aspect of the report.

12. The system of claim 10, wherein the at least one processing device is further programmed to store the report for access by a user of the machine learning model.

13. A computer-implemented method for automatically monitoring a machine learning model for selection of a cohort, the method comprising:
training a machine learning model to select individuals for a cohort, the machine learning model including a neural network and being trained using a training data set of a plurality of labeled medical records, wherein each labeled medical record of the plurality of labeled medical records:
includes a plurality of patient characteristics associated with a corresponding individuals, and
is labeled to indicate a desired outcome for whether the corresponding individual is included in the cohort;
applying the machine learning model to data representing a first plurality of individuals, the data including characteristics of the first plurality of individuals;

based on application of the machine learning model, selecting a subset of the first plurality of individuals as the cohort;

receiving an indication of a characteristic of interest of the plurality of patient characteristics;

determining, based on the data representing the first plurality of individuals, a number of the first plurality of individuals that are associated with the characteristic of interest but are not included in the selected subset;

comparing the number of the first plurality of individuals to a first threshold and a second threshold, the second threshold being greater than the first threshold;

based on a determination that the number of the first plurality of individuals exceeds the first threshold and not the second threshold, transmitting an alert to a user of the machine learning model; and based on a determination that the number of the first plurality of individuals exceeds the first threshold and the second threshold, automatically adjusting at least one aspect of the machine learning model.

* * * * *